United States Patent
Chackerian et al.

(10) Patent No.: US 11,633,471 B2
(45) Date of Patent: Apr. 25, 2023

(54) COMPOSITIONS AND METHODS FOR REDUCING SERUM TRIGLYCERIDES

(71) Applicants: UNM Rainforest Innovations, Albuquerque, NM (US); The United States of America, as represented by the Secretary, Department of Health and Human Services, Bethesda, MD (US); Bryce Chackerian, Albuquerque, NM (US); Alan Remaley, Bethesda, MD (US); Marcelo Amar, Bethesda, MD (US); Alexandra Fowler, Albuquerque, NM (US)

(72) Inventors: Bryce Chackerian, Albuquerque, NM (US); Alan Remaley, Bethesda, MD (US); Marcelo Amar, Bethesda, MD (US); Alexandra Fowler, Albuquerque, NM (US)

(73) Assignees: UNM Rainforest Innovations, Albuquerque, NM (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 61 days.

(21) Appl. No.: 16/977,648

(22) PCT Filed: Mar. 6, 2019

(86) PCT No.: PCT/US2019/020900
§ 371 (c)(1),
(2) Date: Sep. 2, 2020

(87) PCT Pub. No.: WO2019/173438
PCT Pub. Date: Sep. 12, 2019

(65) Prior Publication Data
US 2020/0397891 A1    Dec. 24, 2020

Related U.S. Application Data

(60) Provisional application No. 62/639,274, filed on Mar. 6, 2018.

(51) Int. Cl.
| | | |
|---|---|---|
| A61K 39/385 | (2006.01) | |
| A61K 47/69 | (2017.01) | |
| A61K 39/00 | (2006.01) | |
| A61K 45/06 | (2006.01) | |
| C12N 7/00 | (2006.01) | |

(52) U.S. Cl.
CPC ........ *A61K 39/385* (2013.01); *A61K 39/0012* (2013.01); *A61K 45/06* (2013.01); *A61K 47/6901* (2017.08); *C12N 7/00* (2013.01); *A61K 2039/5258* (2013.01); *A61K 2039/6075* (2013.01); *C12N 2795/18122* (2013.01); *C12N 2795/18123* (2013.01); *C12N 2795/18133* (2013.01)

(58) Field of Classification Search
None
See application file for complete search history.

(56) References Cited

U.S. PATENT DOCUMENTS

| | | | |
|---|---|---|---|
| 5,071,651 | A | 12/1991 | Sabara et al. |
| 5,374,426 | A | 12/1994 | Sabara et al. |
| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,339,068 | B1 | 1/2002 | Krieg et al. |
| 6,949,520 | B1 | 9/2005 | Hartmann et al. |
| 10,279,019 | B2 | 5/2019 | Remaley et al. |
| 10,925,938 | B2 | 2/2021 | Remaley et al. |

FOREIGN PATENT DOCUMENTS

| | | |
|---|---|---|
| EP | 0835318 A2 | 4/1998 |
| EP | 0735898 A1 | 3/1999 |
| EP | 0761231 A1 | 1/2000 |
| WO | 90/03184 | 4/1990 |
| WO | 90/14837 | 12/1990 |
| WO | 92/11291 | 7/1992 |

(Continued)

OTHER PUBLICATIONS

International Search Report and Written Opinion dated Jun. 13, 2019 for PCT/US2019/020900. 7 pages.

(Continued)

*Primary Examiner* — Nicole Kinsey White
(74) *Attorney, Agent, or Firm* — Mueting Raasch Group

(57) ABSTRACT

An immunogen generally includes a virus-like particle and an antigen linked to the virus-like particle. The antigen includes an antigenic portion of a polypeptide, wherein the polypeptide inhibits lipoprotein lipase (LPL) activity by binding to LPL. In some embodiments, the polypeptide is at least a portion of angiopoietin-like 3 (ANGPTL3). In other embodiments, the polypeptide is at least a portion of angiopoietin-like 4 (ANGPTL4). In other embodiments, the polypeptide at least a portion of angiopoietin-like 8 (ANGPTL8). In some embodiments, the virus-like particle is a Qbeta immunogenic carrier. In some of these embodiments, the antigen is linked to the virus-like particle through a Gly-Gly-Gly-Cys linker at the C-terminal of the antigen.

14 Claims, 8 Drawing Sheets
Specification includes a Sequence Listing.

(56) References Cited

FOREIGN PATENT DOCUMENTS

| | | | |
|---|---|---|---|
| WO | 96/02555 | 2/1996 | |
| WO | 96/11711 | 4/1996 | |
| WO | 96/30523 | 10/1996 | |
| WO | 98/15631 | 4/1998 | |
| WO | 98/16247 | 4/1998 | |
| WO | 98/18810 | 5/1998 | |
| WO | 98/36772 | 8/1998 | |
| WO | 98/37919 | 9/1998 | |
| WO | 98/40100 | 9/1998 | |
| WO | 98/52581 | 11/1998 | |
| WO | 98/55495 | 12/1998 | |
| WO | 98/57659 | 12/1998 | |
| WO | 99/11241 | 3/1999 | |
| WO | 99/44636 | 9/1999 | |
| WO | 99/52549 | 10/1999 | |
| WO | 00/07621 | 2/2000 | |
| WO | 00/32227 | 6/2000 | |
| WO | 00/41720 | 7/2000 | |
| WO | 00/48630 | 8/2000 | |
| WO | 00/56358 | 9/2000 | |
| WO | 00/62800 | 10/2000 | |
| WO | 01/21152 | 3/2001 | |
| WO | 01/21207 | 3/2001 | |
| WO | 01/22990 | 4/2001 | |
| WO | 01/85208 | 11/2001 | |
| WO | 02/056905 | 7/2002 | |
| WO | 03/024480 | 3/2003 | |
| WO | 03/024481 | 3/2003 | |
| WO | 06/134423 | 12/2006 | |
| WO | 07/026190 | 3/2007 | |
| WO | 2017/027316 | 2/2017 | |
| WO | 2017/205454 | 11/2017 | |
| WO | WO-2017205454 A1 * | 11/2017 | ......... A61K 39/0005 |
| WO | 2019/173438 | 9/2019 | |

OTHER PUBLICATIONS

International Preliminary Report on Patentability dated Sep. 8, 2020 for PCT/US2019/020900. 5 pages.

Yuan et al., Subtype-independent immature secretion and subtype-dependent replication deficiency of a highly frequent, naturally occurring mutation of human hepatitis B virus core antigen. J Virol 73, 10122-10128 (1999).

Powell & Newman, Vaccine Design: The Subunit and Adjuvant Approach. Plenum Press, New York, NY; 1995. Chapter 10.

Yi et al., CpG oligodeoxyribonucleotides rescue mature spleen B cells from spontaneous apoptosis and promote cell cycle entry. J Immunol 160, 5898-5906 (1998).

Yi et al., CpG DNA rescue of murine B lymphoma cells from anti-IgM-induced growth arrest and programmed cell death is associated with increased expression of c-myc and bcl-xL. J Immunol 157, 4918-4925 (1996).

Ballas et al., Induction of NK activity in murine and human cells by CpG motifs in oligodeoxynucleotides and bacterial DNA. J Immunol 157, 1840-1845 (1996).

Chu et al., CpG oligodeoxynucleotides act as adjuvants that switch on T helper (Th1) immunity. J Exp Med 186, 1623-1631 (1997).

Cowdery et al., Bacterial DNA induces NK cells to produce IFN-gamma in vivo and increases the toxicity of ipopolysaccharides. J Immunol 156, 4570-4575 (1996).

Davis et al., CpG DNA is a potent enhancer of specific immunity in mice immunized with recombinant hepatitis B surface antigen. J Immunol 160, 870-876 (1998).

Geldenhuys et al., Emerging strategies of targeting lipoprotein lipase for metabolic and cardiovascular diseases. Drug Discov Today 22, 352-365 (2017).

Golmohammadi et al., The crystal structure of bacteriophage Q beta at 3.5 A resolution. Structure 4, 543-554 (1996).

Haller et al., ANGPTL8 requires ANGPTL3 to inhibit lipoprotein lipase and plasma triglyceride clearance. J Lipid Res 58, 1166-1173 (2017).

Halpern et al., Bacterial DNA induces murine interferon-gamma production by stimulation of interleukin-12 and tumor necrosis factor-alpha. Cell Immunol 167, 72-78 (1996).

Kanzler et al., Therapeutic targeting of innate immunity with Toll-like receptor agonists and antagonists. Nat Med 13, 552-559 (2007).

Klinman et al., CpG motifs present in bacteria DNA rapidly induce lymphocytes to secrete intedeukin 6, intedeukin 12, and interferon gamma. Proc Natl Acad Sci U S A 93, 2879-2883 (1996).

Kozlovska et al., Recombinant RNA phage Q beta capsid particles synthesized and self-assembled in *Escherichia coli*. Gene 137, 133-137 (1993).

Kozlovska et al., RNA phage Q beta coat protein as a carrier for foreign epitopes. Intervirology 39, 9-15 (1996).

Krieg, Immune effects and mechanisms of action of CpG motifs. Vaccine 19, 618-622 (2001).

Yi et al., CpG motifs in bacterial DNA activate leukocytes through the pH-dependent generation of reactive oxygen species. J Immunol 160, 4755-4761 (1998).

Krieg et al., CpG motifs in bacterial DNA trigger direct B-cell activation. Nature 374, 546-549 (1995).

Lee et al., Identification of a new functional domain in angiopoietin-like 3 (ANGPTL3) and angiopoietin-like 4 (ANGPTL4) involved in binding and inhibition of lipoprotein lipase (LPL). J Biol Chem 284, 13735-13745 (2009).

Lipford et al., CpG-containing synthetic oligonucleotides promote B and cytotoxic T cell responses to protein antigen: a new class of vaccine adjuvants. Eur J Immunol 27, 2340-2344 (1997).

Matsui et al., The isolation and characterization of a Norwalk virus-specific cDNA. J Clin Invest 87, 1456-1461 (1991).

Yi et al., Rapid immune activation by CpG motifs in bacterial DNA. Systemic induction of IL-6 transcription through an antioxidant-sensitive pathway. J Immunol 157, 5394-5402 (1996).

Messina et al., Stimulation of in vitro murine lymphocyte proliferation by bacterial DNA. J Immunol 147, 1759-1764 (1991).

Moldoveanu et al., CpG DNA, a novel immune enhancer for systemic and mucosal immunization with influenza virus. Vaccine 16, 1216-1224 (1998).

Roman et al., Immunostimulatory DNA sequences function as T helper-1-promoting adjuvants. Nat Med 3, 849-854 (1997).

Sasnauskas et al., Yeast cells allow high-level expression and formation of polyomavirus-like particles. Biol Chem 380, 381-386 (1999).

Sjolander et al., ISCOMs: an adjuvant with multiple functions. J Leukoc Biol 64, 713-723 (1998).

Stacey et al., Macrophages ingest and are activated by bacterial DNA. J Immunol 157, 2116-2122 (1996).

Tatusova et al., BLAST 2 Sequences, a new tool for comparing protein and nucleotide sequences. FEMS Microbiol Lett 174, 247-250 (1999).

Twomey et al., Structure and immunogenicity of experimental foot-and-mouth disease and poliomyelitis vaccines. Vaccine 13, 1603-1610 (1995).

Ulrich et al., Core particles of hepatitis B virus as carrier for foreign epitopes. Adv Virus Res 50, 141-182 (1998).

Warnes et al., Expression of the measles virus nucleoprotein gene in *Escherichia coli* and assembly of nucleocapsid-like structures Gene 160, 173-178 (1995).

Weiner et al., Immunostimulatory oligodeoxynucleotides containing the CpG motif are effective as immune adjuvants in tumor antigen immunization. Proc Natl Acad Sci U S A 94, 10833-10837 (1997).

Xi et al., Norwalk virus genome cloning and characterization. Science 250, 1580-1583 (1990).

Yamamoto et al., In vitro augmentation of natural killer cell activity and production of interferon-alpha/beta and -gamma with deoxyribonucleic acid fraction from *Mycobacterium bovis* BCG. Jpn J Cancer Res 79, 866-873 (1988).

(56) References Cited

OTHER PUBLICATIONS

Yamamoto et al., Unique palindromic sequences in synthetic oligonucleotides are required to induce IFN [correction of INF] and augment IFN-mediated [correction of INF] natural killer activity. J Immunol 148, 4072-4076 (1992).

* cited by examiner

```
              1         10        20        30        40        50        60        70        80  85
Mm. Angpt13   MHTIKLFLFVVPLVIASRVDPDLSSFDSAPSEPKS-RFAMLDDVKILANGLLQLGHGLKDFVHKTKGQINDIFQKLNIFDQSFYD
Hs. Angpt13   MFTIKLLLFIVPLVISSRIDQNSSFDSLSPEPKS-RFAMLDDVKILANGLLQLGHGLKDFVHKTKGQINDIFQKLNIFDQSFYD
Mm. Angpt14   ---MRCAPTAGAALVLCAATAGLLSAQGRPAQPEPPRFASWDEMNLLAHGLLQLGHGLREHVERTRGQLGALERRMAACGNACQG
Hs. Angpt14   ---MSGAPTAGAALMLCAATAVLLSAQGGPVQSKSPRFASWDEMNVLAHGLLQLGQGLREHAERTRSQLSALERRLSACGSACQG
```

(B)

Long: ³²EPKSRFAMLDDVKILANGLLQLGH⁵⁵

1: ³²EPKSRFAMLDDVKILA⁴⁷

2: ³⁹MLDDVKILANGLLQLGH⁵⁵

3: ³⁶RFAMLDDVKILANGLL⁵¹

(C)

Long: ²⁹QPEPPRFASWDEMNLLAHGLLQLGH⁵³

FIG. 2
(A)
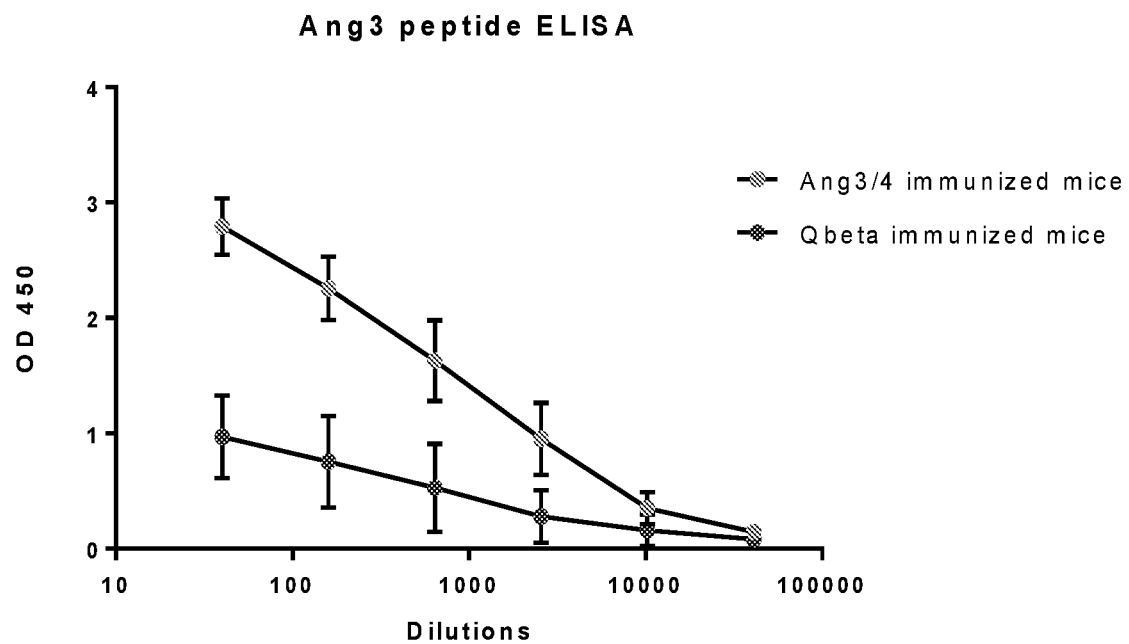
(B)
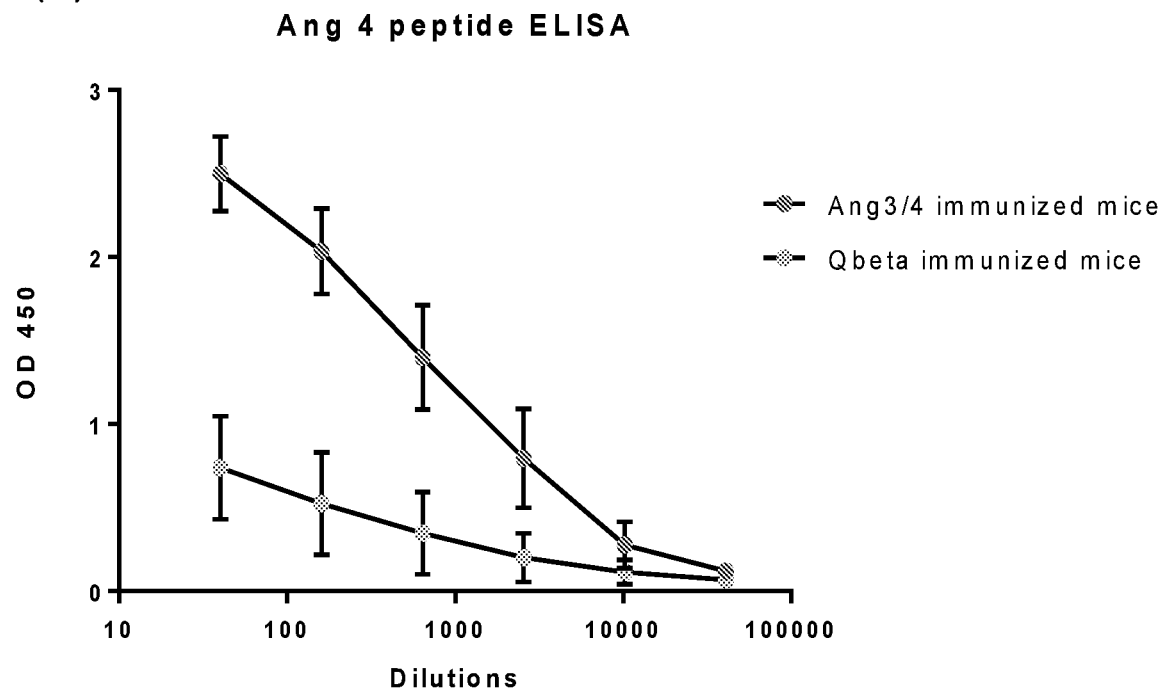

FIG. 8

```
ANGPTL3  MFTIKLLLFIVPLVISSRIDQDNSSFDSLSPEPKS-REAMLDDVKILANGLLQLGHGLKDFVHKTKGQIND
ANGPTL4  --MSGAPTAGAALMLCAATAVLLSAQGGPVQSKSPRFASWDEMNVLAHGLLQLGQGLREHAERTRSQLSAL
ANGPTL8  -------MPVPALCLLWALAMVTRPASAAPMGGPELAQHEELTLLFHGTLQLGQALNGVYRTTEGRLTKA
```

COMPOSITIONS AND METHODS FOR REDUCING SERUM TRIGLYCERIDES

CROSS-REFERENCE TO RELATED APPLICATION

This application is the § 371 U.S. National Stage of International Application No. PCT/US2019/020900, filed Mar. 6, 2019, which claims the benefit of U.S. Provisional Patent Application No. 62/639,274, filed Mar. 6, 2018, each of which is incorporated herein by reference in its entirety.

GOVERNMENT FUNDING

This invention was made with government support under HL131696 awarded by National Institutes of Health. The government has certain rights in the invention.

SEQUENCE LISTING

This application contains a Sequence Listing electronically submitted to the United States Patent and Trademark Office via EFS-Web as an ASCII text file entitled "SEQ Listing 310-000130US01_ST25.txt" having a size of 10.9 kilobytes and created on Sep. 2, 2020. Due to the electronic filing of the Sequence Listing, the electronically submitted Sequence Listing serves as both the paper copy required by 37 CFR § 1.821 (c) and the CRF required by § 1.821 (e).

SUMMARY

This disclosure describes, in one aspect, an immunogen that generally includes a virus-like particle and an antigen linked to the virus-like particle. The antigen includes an antigenic portion of a polypeptide, wherein the polypeptide inhibits lipoprotein lipase (LPL) activity by binding to LPL.

In some embodiments, the polypeptide includes at least a portion of angiopoietin-like 3 (ANGPTL3) such as, for example, a polypeptide having at least 80% amino acid similarity to amino acids 32-47 of SEQ ID NO:1 or at least 80% amino acid similarity to amino acids 32-57 of SEQ ID NO:1. In some of these embodiments, the polypeptide can have at least 80% amino acid identity to amino acids 32-47 of SEQ ID NO:1 or at least 80% amino acid identity to amino acids 32-57 of SEQ ID NO:1.

In some embodiments, the polypeptide includes at least a portion of angiopoietin-like 4 (ANGPTL4) such as, for example, a polypeptide having at least 80% sequence similarity to amino acids 29-45 of SEQ ID NO:2 or at least 80% sequence similarity to amino acids 29-55 of SEQ ID NO:2. In some of these embodiments, the polypeptide can have at least 80% sequence identity to amino acids 29-45 of SEQ ID NO:2 or at least 80% sequence identity to amino acids 29-55 of SEQ ID NO:2.

In some embodiments, the polypeptide includes at least a portion of angiopoietin-like 8 (ANGPTL8) such as, for example, a polypeptide having at least 80% sequence similarity to amino acids 23-49 of SEQ ID NO:3 or at least 80% sequence similarity to amino acids 23-39 of SEQ ID NO:3. In some of these embodiments, the polypeptide can have at least 80% sequence similarity to amino acids 23-49 of SEQ ID NO:3 or at least 80% sequence identity to amino acids 23-39 of SEQ ID NO:3.

In some embodiments, the virus-like particle is a Qbeta immunogenic carrier. In some of these embodiments, the antigen is linked to the virus-like particle through a Gly-Gly-Gly-Cys linker at the C-terminal of the antigen.

In another aspect, this disclosure describes a composition that includes any embodiments of the immunogen summarized above and a pharmaceutically-acceptable carrier. In some embodiments, the composition can further include an adjuvant.

In another aspect, this disclosure describes a method of reducing serum triglycerides in a subject. Generally, the method includes administering to the subject a therapeutically effective amount of any embodiment of the immunogen summarized above.

In some embodiments, the immunogen is administered in combination with an adjuvant.

In some embodiments, the immunogen is administered in combination with at least one additional therapeutic agent. In some of these embodiments, the additional therapeutic agent can be a statin or a fabric acid derivative.

In another aspect, this disclosure describes a nucleic acid encoding any embodiment of the immunogen summarized above.

In another aspect, this disclosure describes an expression vector that includes a nucleic acid encoding any embodiment of the immunogen summarized above.

In another aspect, this disclosure describes a host cell that includes an expression vector that includes a nucleic acid encoding any embodiment of the immunogen summarized above.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. LPL-inhibiting domains of angiopoietin-like 3 (ANGPTL3) and angiopoietin-like 4 (ANGPTL4). (A) Alignment of amino acids sequences of mouse ANGPTL3 (Mm.Angptl3; SEQ ID NO:4), human ANGPTL3 (Hs. Angptl3; amino acids 1-84 of SEQ ID NO:1), mouse ANGPTL4 (Mm.Angptl4; SEQ ID NO:5), and human ANGPTL4 (Hs. Angptl4; amino acids 1-82 of SEQ ID NO:2). (B) ANGPTL3 amino acid sequences used for antigen display. Long: amino acids 32-55 of SEQ ID NO:1; #1: amino acids 32-47 of SEQ ID NO:1; #2: amino acids 39-55 of SEQ ID NO:1; #3: amino acids 36-51 of SEQ ID NO:1. #1 shows the mouse ANGPTL3 LPL-inhibiting domain (positions 32-47). (C) ANGPTL4 amino acid sequence (amino acids 29-52 of SEQ ID NO:2) used for antigen display.

FIG. 2. Immunogenicity of pooled Ang3 and Ang4 VLPs. (A) Ang3 peptide ELISA. (B) Ang4 peptide ELISA.

FIG. 8. Amino acid sequences of ANGPTL3 (amino acids 1-70 of SEQ ID NO:1), ANGPTL4 (amino acids 1-69 of SEQ ID NO:2), and ANGPTL8 (amino acids 1-63 of SEQ ID NO:3). Epitopes are shown in the box: amino acids 32-57 of SEQ ID NO:1, amino acids 29-49 of SEQ ID NO:2, and amino acids 24-55 of SEQ ID NO:3. Underlined sequence corresponds to Sequence #1 in FIG. 1B.

DETAILED DESCRIPTION OF ILLUSTRATIVE EMBODIMENTS

Elevated serum triglycerides is a risk factor for cardiovascular disease. Plasma triglycerides (TGs) are metabolized by the enzyme lipoprotein lipase (LPL), which catalyzes the hydrolysis of TGs into free fatty acids, which are either re-esterified for storage or oxidized for fuel.

The secreted proteins angiopoietin-like 3 (ANGPTL3) and angiopoietin-like 4 (ANGPTL4) and angiopoietin-like 8 (ANGPTL8) regulate LPL activity by binding and inactivating LPL. Inhibiting ANGPTL3, ANGPTL4, and/or ANGPTL8 can dramatically affect TG levels. ANGPTL3 and ANGPTL4 knockout mice exhibit reduced lipid levels, and treatment with monoclonal antibodies targeting ANGPTL3, ANGPTL4, or ANGPTL8 can lower serum TG levels. In humans, loss-of-function mutations in ANGPTL3 are associated with low TG levels and hypolipidemia.

Displaying target antigens on the surface of a virus-like particle (VLP) can dramatically increase immunogenicity of the antigen. VLP display can even be used to elicit strong antibody responses against self-antigens, which are normally poorly immunogenic. This disclosure reports using VLP display to develop vaccines targeting ANGPTL3 and ANGPTL4. ANGPTL peptides representing a domain important for binding LPL were synthesized and conjugated to Qβ bacteriophage VLPs. Four ANGPTL3 peptides (amino acids 32-55, amino acids 32-47, amino acids 39-55, or amino acids 36-51 of SEQ ID NO:1, FIG. 1B) and one ANGPTL4 peptide (amino acids 29-52 of SEQ ID NO:2, FIG. 1C) were synthesized to include a C-terminal Gly-Gly-Gly-Cys to allow conjugation to Qβ VLPs. All of the peptides except ANGPTL3 (32-55) were successfully conjugated to Qβ using standard methods.

Mice were immunized intramuscularly with three doses of 5 µg of ANGPTL-VLPs or, as a control, wild-type Qβ VLPs. Plasma was collected and peptide IgG levels were determined by ELISA. VLPs displaying ANGPTL3 (amino acids 32-47 of SEQ ID NO:1) and ANGPTL4 (amino acids 29-52 of SEQ ID NO:2) elicited high titer antibody responses, whereas antibody responses mice immunized with the other vaccines were low (data not shown). To assess the effects of immunization on TG levels, mice were immunized with Qβ-ANGPTL3 (amino acids 32-47 of SEQ ID NO:1), Qβ-ANGPTL4 (amino acids 29-52 of SEQ ID NO:2), a mixture of the two vaccines (5 µg of each), or wild-type Qβ VLPs (as controls). Antibody levels in the group immunized with the mixture of vaccines are shown in FIG. 2.

Figure 7:
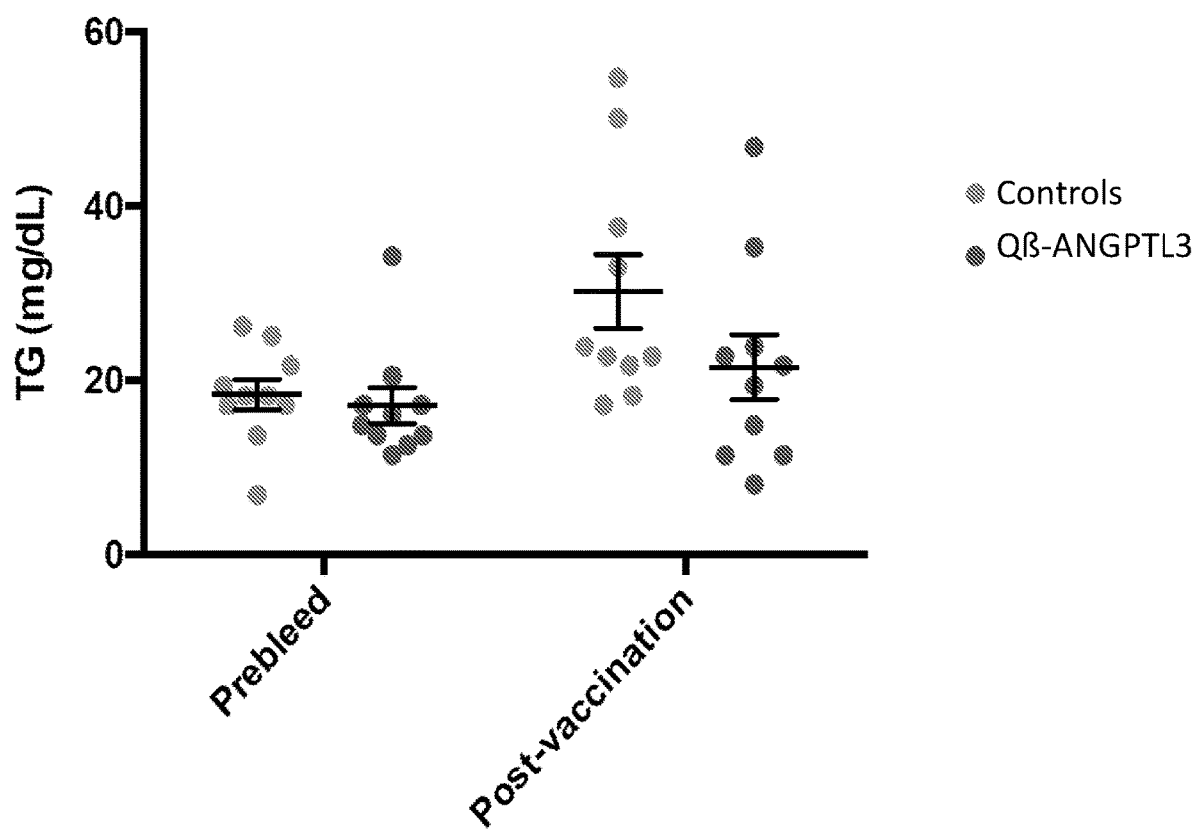
FIG. 7. Triglyceride (TG) levels in mice immunized with Qβ-ANGPTL3 versus wild-type Qβ VLPs. Mice were immunized three times (at three-week intervals) and sera was collected prior to immunization (at prebleed) and two weeks after the final vaccination. TG levels were measured enzymatically using a ChemWell instrument.

FIG. 7 shows triglyceride levels in mice immunized with Qβ-ANGPTL3 versus wild-type Qβ VLPs. Mice were immunized three times (at three-week intervals) and sera were collected prior to immunization and two weeks after the final vaccination. Vaccinated mice have lower steady state levels of TGs.

Figure 3:
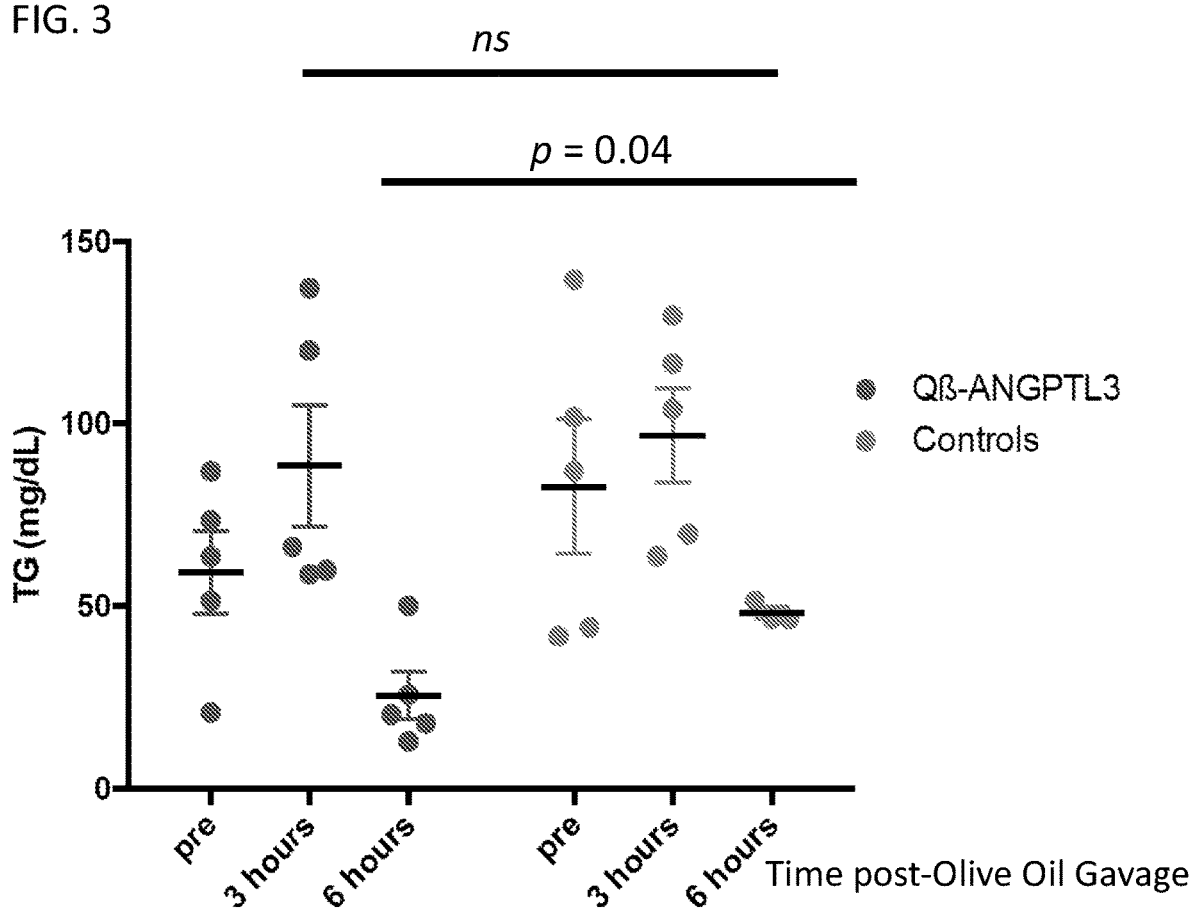
FIG. 3. Triglyceride Levels in Mice Immunized with Qβ-ANGPTL3.
Figure 4:
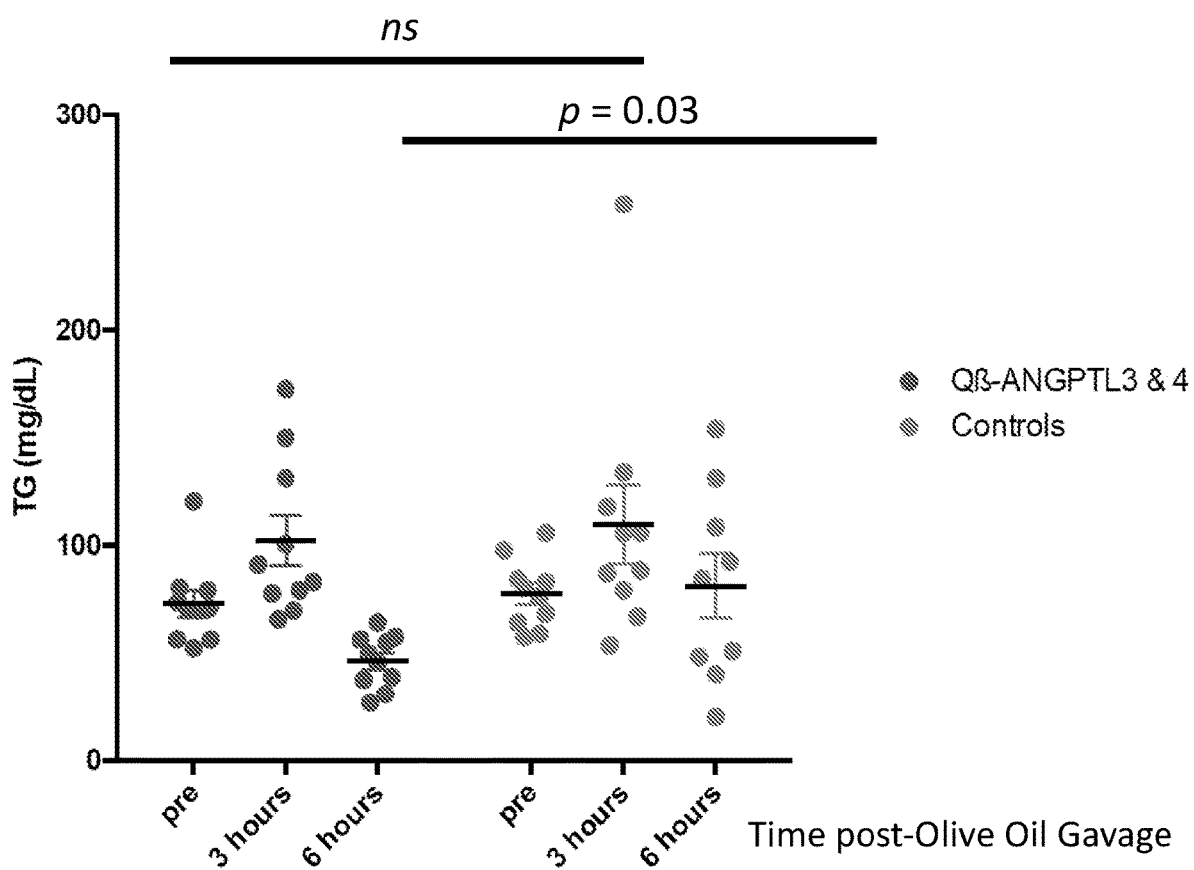
FIG. 4. Triglyceride Levels in Mice Immunized with Qβ-ANGPTL3+Qβ-ANGPTL4.
Figure 5:
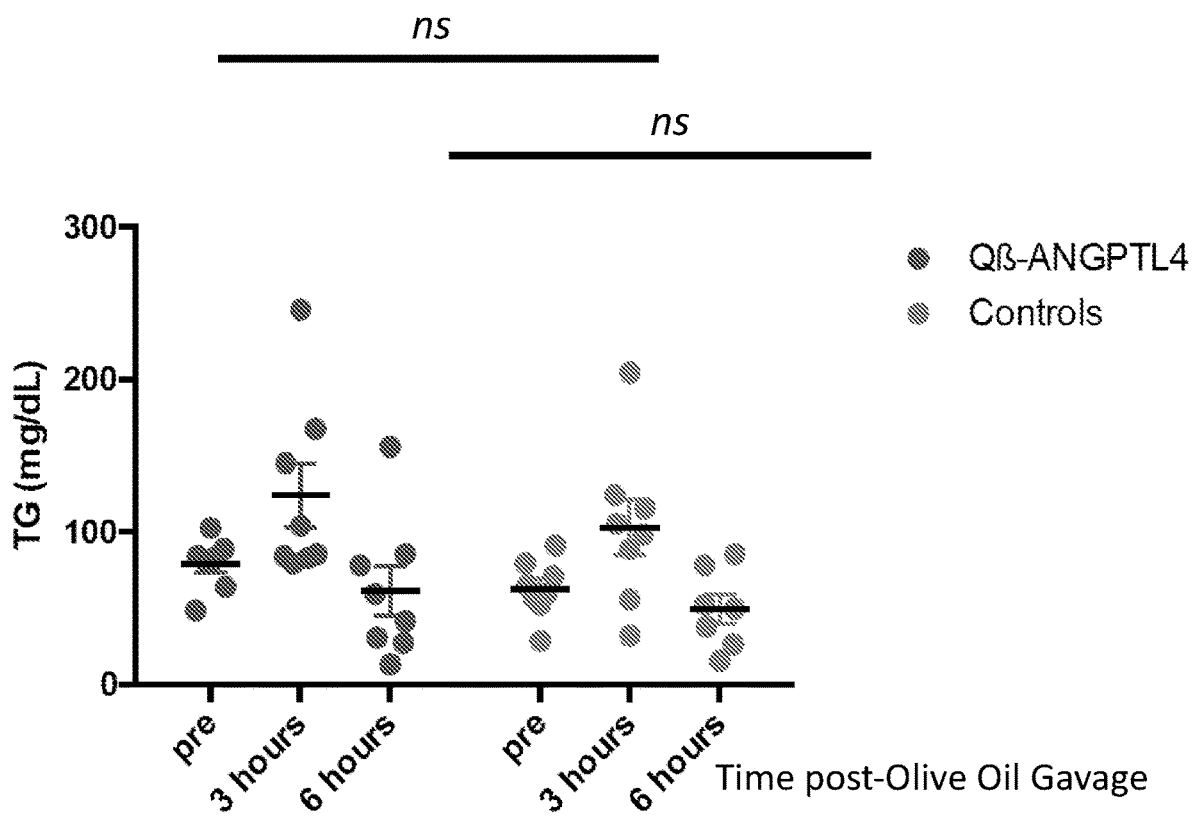
FIG. 5. Triglyceride Levels in Mice Immunized with Qβ-ANGPTL4.
Figure 6:
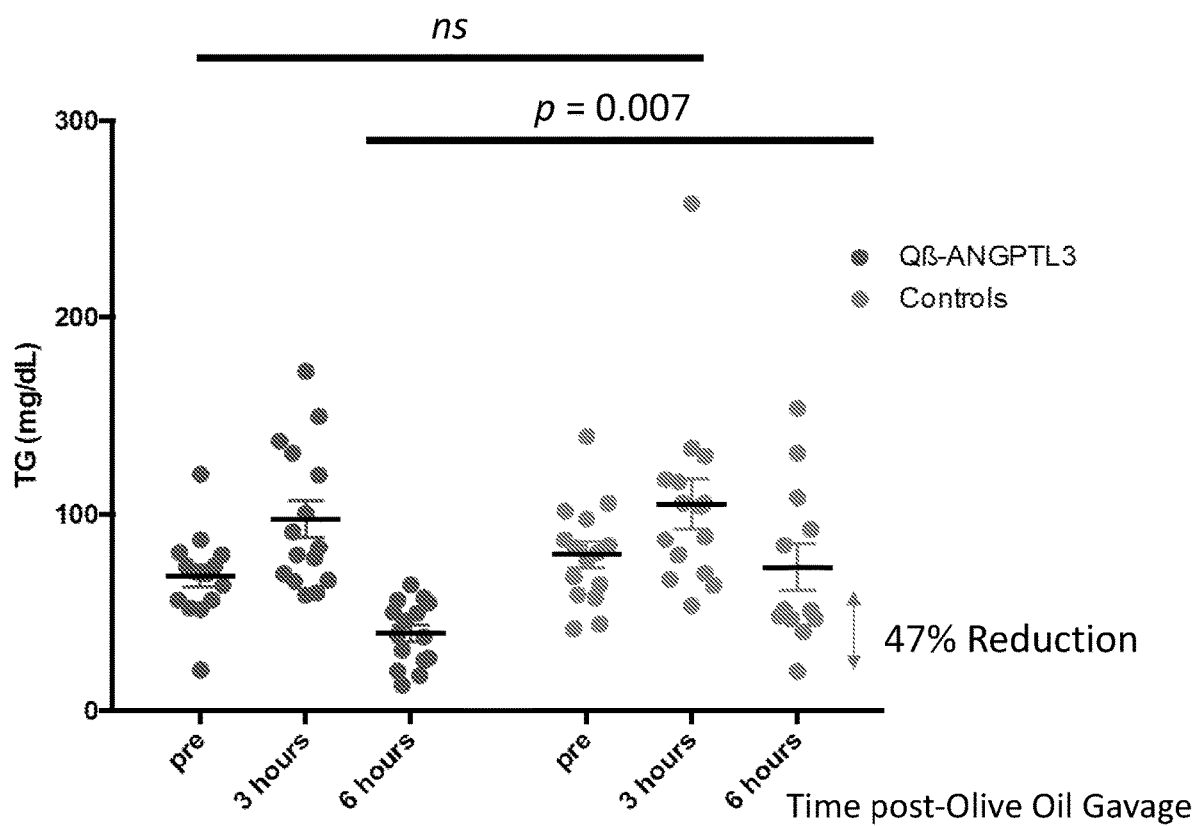
FIG. 6. Aggregated Data in all mice immunized with Qβ-ANGPTL3.

In a subsequent experiment, mice were immunized three times, fasted, and then given an olive oil gavage, which temporarily elevates TG levels. Mice immunized with Qβ-ANGPTL3 (amino acids 32-47 of SEQ ID NO:1) (FIG. 3), the mixed vaccine (FIG. 4), but not Qβ-ANGPTL4 (amino acids 29-52 of SEQ ID NO:2) (FIG. 5), showed a significant reduction (~50%) in TG levels six hours after the gavage. FIG. 6 compares all mice that received the Qβ-ANGPTL3 (amino acids 32-47 of SEQ ID NO:1) vaccine (with or without Qβ-ANGPTL4) relative to controls. Taken together, these data show that a vaccine targeting ANGPTL can reduce TG levels in mice.

Thus, this disclosure describes an immunogen that generally includes a virus-like particle and, linked to the virus-like particle, an antigen that includes an antigenic portion of a polypeptide in which the polypeptide inhibits lipoprotein lipase (LPL) activity by binding to LPL. In some embodiments, the antigen can include an amino acid sequence that is, or is structurally similar to, amino acids 32-47 of human ANGPTL3 (SEQ ID NO:1), amino acids 32-55 of human ANGPLT3 (SEQ ID NO:1), amino acids 29-52 of human ANGPTL4 (SEQ ID NO:2), or amino acids 23-49 of human ANGPTL8 (SEQ ID NO:3).

As used herein, a polypeptide is "structurally similar" to a reference polypeptide if the amino acid sequence of the polypeptide possesses a specified amount of identity compared to the reference polypeptide. Structural similarity of two polypeptides can be determined by aligning the residues of the two polypeptides (for example, a candidate polypeptide compared to either amino acids 32-47 of human ANGPTL3 (SEQ ID NO:1), amino acids 32-55 of human ANGPLT3 (SEQ ID NO:1), amino acids 29-52 of human ANGPTL4 (SEQ ID NO:2), or amino acids 23-49 of human ANGPTL8 (SEQ ID NO:3)) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide, the reference polypeptide being, e.g., amino acids 32-47 of human ANGPTL3 (SEQ ID NO:1), amino acids 32-55 of human ANGPLT3 (SEQ ID NO:1), amino acids 29-52 of human ANGPTL4 (SEQ ID NO:2), or amino acids 23-49 of human ANGPTL8 (SEQ ID NO:3). A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in the antigen may be selected from other members of the class to which the substituted amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$. Likewise, biologically active analogs of a polypeptide containing deletions or additions of one or more contiguous or noncontiguous amino acids that do not eliminate a functional activity of the polypeptide are also contemplated.

Thus, the antigen can have an amino sequence with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to the reference amino acid sequence (e.g., amino acids 32-47 of human ANGPTL3 (SEQ ID NO:1), amino acids 32-55 of human ANGPLT3 (SEQ ID NO:1), amino acids 29-52 of human ANGPTL4 (SEQ ID NO:2), or amino acids 23-49 of human ANGPTL8 (SEQ ID NO:3)).

In some cases, the antigen can have an amino acid sequence with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the reference amino acid sequence (e.g., amino acids 32-47 of human ANGPTL3 (SEQ ID NO:1), amino acids 32-55 of human ANGPLT3 (SEQ ID NO:1), amino acids 29-52 of human ANGPTL4 (SEQ ID NO:2), or amino acids 23-49 of human ANGPTL8 (SEQ ID NO:3)).

An antigen (e.g., an ANGPTL polypeptide) also can be designed to provide additional sequences, such as, for example, the addition of added C-terminal or N-terminal amino acids that can, for example, facilitate purification (e.g., by trapping on columns or use of antibodies) or linking to the virus-like particle. Such tags include, for example, histidine-rich tags that allow purification of polypeptides on nickel columns. Such gene modification techniques and suitable additional sequences are well known in the molecular biology arts.

As used herein, the term "virus-like particle" refers to a structure resembling a virus particle, but is nonpathogenic. In general, virus-like particles lack at least part of the viral genome. Also, virus-like particles can often be produced in large quantities by heterologous expression and can be easily purified. A virus-like particle used to make an immunogen as described herein may contain nucleic acid distinct from their genome. An exemplary virus-like particles suitable for use to prepare the immunogens described herein is a viral capsid such as the viral capsid of the corresponding virus, bacteriophage, or RNA-phage.

As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition, however, encompasses virus-like particles of bacteriophages, in which the aforementioned gene or genes are still present but inactive, and, therefore, also leading to non-replicative and noninfectious virus-like particles of a bacteriophage. The capsid structure formed from the self-assembly of subunits of RNA phage coat protein and optionally containing host RNA is herein referred to as a "VLP of RNA phage coat protein." Specific examples are the VLP of Qbeta, MS2, PP7 or AP205 coat proteins. In the specific case of Qbeta coat protein, for example, the VLP may either be assembled exclusively from Qbeta CP subunits (generated by expression of a Qbeta CP gene containing a TAA stop codon precluding any expression of the longer A1 protein through suppression (Kozlovska et al., 1996 Intervirology 39: 9-15), or additionally contain A1 protein subunits in the capsid assembly. Generally, the percentage of Qbeta A1 protein relative to Qbeta CP in the capsid assembly will be limited, in order to ensure capsid formation.

Examples of VLPs suitable as immunogenic carriers in the context of the immunogens described herein include, but are not limited to, VLPs of Qbeta, MS2, PP7, AP205 and other bacteriophage coat proteins, the capsid and core proteins of Hepatitis B virus (Ulrich, et al., Virus Res. 50: 141-182 (1998)), measles virus (Warnes, et al., Gene 160: 173-178 (1995)), Sindbis virus, rotavirus (U.S. Pat. Nos. 5,071,651 and 5,374,426), foot-and-mouth-disease virus (Twomey, et al., Vaccine 13: 1603-1610, (1995)), Norwalk virus (Jiang, X., et al., Science 250: 1580-1583 (1990); Matsui, S. M., et al., J. Clin. Invest. 87: 1456-1461 (1991)), the retroviral GAG protein (PCT Patent Appl. No. WO 96/30523), the retrotransposon Ty protein pl, the surface protein of Hepatitis B virus (WO 92/11291), human papilloma virus (WO 98/15631), human polyoma virus (Sasnauskas K., et al., Biol. Chem. 380 (3): 381-386 (1999); Sasnauskas K., et al., Generation of recombinant virus-like particles of different polyomaviruses in yeast. 3rd International Workshop "Virus-like particles as vaccines." Berlin, Sep. 26-29 (2001)), RNA phages, Ty, frphage, GA-phage, AP 205-phage and, in particular, Qbeta-phage, Cowpea chlorotic mottle virus, cowpea mosaic virus, human papilloma viruses (HPV), bovine papilloma viruses, porcine parvovirus, parvoviruses such as B19, porcine (PPV) and canine (CPV) parvovirues, caliciviruses (e.g., Norwalk virus, rabbit hemorrhagic disease virus [RHDV]), animal hepadnavirus core Antigen VLPs, filamentous/rod-shaped plant viruses, including but not limited to Tobacco Mosaic Virus (TMV), Potato Virus X (PVX), Papaya Mosaic Virus (PapMV), Alfalfa Mosaic Virus (AIMV), and Johnson Grass Mosaic Virus (JGMV), insect viruses such as flock house virus (FHV) and tetraviruses, polyomaviruses such as Murine Polyomavirus (MPyV), Murine Pneumotropic Virus (MPtV), BK virus (BKV), cowpea mosaic virus, T7 bacteriophage, and JC virus (JCV).

As will be readily apparent to those skilled in the art, the VLP to be used as an immunogenic carrier is not limited to any specific form. The particle can be synthesized chemically or through a biological process, which can be natural or non-natural. By way of example, this type of embodiment includes a virus-like particle or a recombinant form thereof.

In a more specific embodiment, the VLP can include, or alternatively consist of, recombinant polypeptides of any of the virus known to form a VLP. The virus-like particle can further include, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts. Variant VLPs suitable for use in preparing an immunogen as described herein can be derived from any organism so long as they are able to form a "virus-like particle" and can be used as an "immunogenic carrier" as defined herein.

A VLP used to prepare an immunogen as described herein may include the capsid protein or surface antigen of HBV (HBcAg and HBsAg respectively) or recombinant proteins or fragments thereof, and the coat proteins of RNA-phages or recombinant proteins or fragments thereof, more preferably the coat protein of Qbeta or recombinant proteins or fragments thereof. In one embodiment, the immunogenic carrier used in combination with an antigenic polypeptide (e.g., an ANGPTL polypeptide) is an HBcAg protein. Examples of HBcAg proteins that can be used to produce an immunogen as described herein can be readily determined by one skilled in the art. Examples include, but are limited to, HBV core proteins described in Yuan et al., (J. Virol. 73: 10122-10128 (1999)), and in WO00/198333, WO 00/177158, WO 00/214478, WO WO00/32227, WO01/85208, WO02/056905, WO03/024480, and WO03/024481. HBcAgs suitable for preparing an immunogen as described herein can be derived from any organism so long as they are able to form a "virus-like particle" and can be used as an "immunogenic carrier" as defined herein.

In specific embodiments, the immunogenic carrier used in combination with an antigenic ANGPTL polypeptide is a Qbeta coat protein. Qbeta coat protein was found to self-assemble into capsids when expressed in $E.$ $coli$ (Kozlovska et al., 1993 Gene 137:133-137). The obtained capsids or virus-like particles showed an icosahedral phage-like capsid structure with a diameter of 25 nm and T=3 quasi symmetry. Further, the crystal structure of phage Qss has been solved. The capsid contains 180 copies of the coat protein, which are linked in covalent pentamers and hexamers by disulfide bridges (Golmohammadi et al., 1996 Structure 4: 5435554) leading to a remarkable stability of the capsid of Qbeta coat protein. Qbeta capsid protein also shows unusual resistance to organic solvents and denaturing agents. The high stability of the capsid of Qbeta coat protein is an advantageous feature, in particular, for its use in immunization and vaccination of mammals and humans in accordance with the methods described herein.

Examples of Qbeta coat proteins that can be used to prepare an immunogen as described herein can be readily determined by one skilled in the art. Examples have been extensively described in International Patent Application Publication nos. WO02/056905, WO03/024480, WO03/024481 (incorporated herein by reference in their entirety) and include, but are not limited to, amino acid sequences disclosed in PIR database, accession No. VCBPQbeta referring to Qbeta CP; Accession No. AAA16663 referring to Qbeta A1 protein; and variants thereof including variants proteins in which the N-terminal methionine is cleaved; C-terminal truncated forms of Qbeta A1 missing as much as 100, 150 or 180 amino acids; variant proteins which have been modified by the removal of a lysine residue by deletion or substitution or by the addition of a lysine residue by substitution or insertion (see for example Qbeta-240, Qbeta-243, Qbeta-250, Qbeta-251 and Qbeta-259 disclosed in PCT publication No. WO 03/024481, incorporated by reference in its entirety), and variants exhibiting at least 80%, 85%, 90%, 95%, 97%, or 99% identity to any of the Qbeta core proteins described above. Variant Qbeta coat proteins suitable for preparing an immunogen as described herein can be derived from any organism so long as they are able to form a "virus-like particle" and can be used as "immunogenic carriers" as defined herein.

In some embodiments, an immunogenic composition that includes the immunogen described herein can further include an adjuvant. Suitable adjuvants include those suitable for use in mammals, preferably in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al. (1998) J. Leukocyte Biol. 64:713; WO90/03184, WO96/11711, WO 00/48630, WO98/36772, WO00/41720, WO06/134423 and WO07/026,190), LT/CT mutants, poly (D,L-lactide-co-glycolide) (PLG) microparticles, Quil A, saponin-based adjuvants, TiterMax classic, TiterMax Gold, interleukins, and the like. For veterinary applications including but not limited to animal experimentation, one can use Freund's adjuvant, N-acetyl-muramyl-L-threonyl-D-isoglutamine (thr-MDP), N-acetyl-nor-muramyl-L-alanyl-D-isoglutamine (CGP 11637, referred to as nor-MDP), N-acetyl-muramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in Vaccine design: the subunit and adjuvant approach, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON (Cambridge Bioscience, Worcester, Mass.), ABISCO (Isconova, Sweden), or ISCOMATRIX (Commonwealth Serum Laboratories, Australia), may be used or particles generated therefrom such as ISCOMs (immunostimulating complexes), which ISCOMS may be devoid of additional detergent e.g., WO00/07621; (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (WO99/44636), etc.), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) e.g., GB-2220221, EP-A-0689454, optionally in the substantial absence of alum when used with pneumococcal saccharides e.g., WO00/56358; (6) combinations of 3dMPL with, for example, QS21 and/or oil-in-water emulsions e.g., EP-A-0835318, EP-A-0735898, EP-A-0761231; (7) oligonucleotides including CpG motifs [Krieg Vaccine 2000, 19, 618-622; Krieg Curr opin Mol Ther 2001 3:15-24; Roman et al., Nat. Med., 1997, 3, 849-854; Weiner et al., PNAS USA, 1997, 94, 10833-10837; Davis et al, J. Immunol, 1998, 160, 870-876; Chu et al., J. Exp. Med, 1997, 186, 1623-1631; Lipford et al, Ear. J. Immunol., 1997, 27, 2340-2344; Moldoveami et al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157, 4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g., WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g., a CpG oligonucleotide) (WO00/62800); (11) an immunostimulant and a particle of metal salt e.g., WO00/23105; (12) a saponin and an oil-in-water emulsion e.g., WO99/11241; (13) a saponin (e.g., QS21)+3dMPL+IM2 (optionally+a sterol) e.g., WO98/57659; (14) other substances that act as immunostimulating agents to enhance the efficacy of the composition, such as Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g., as described in Kanzler et al 2007, Nature Medicine 13, p1552-9), including TLR3 ligands such as polyI:C and similar compounds such as Hiltonol and Ampligen.

In a particular embodiment, the adjuvant is an immunostimulatory oligonucleotide and more preferably a CpG oligonucleotide. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may include one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail below. Therapeutic methods described herein embrace the use of these different classes of CpG immunostimulatory oligonucleotides.

Any of the classes may be subjugated to an E modification that enhances its potency. An E modification may be a halogen substitution for the 5' terminal nucleotide; examples of such substitutions include but are not limited to bromo-uridine or iodo-uridine substitutions. An E modification can also include an ethyl-uridine substitution for the 5' terminal nucleotide.

The "A class" CpG immunostimulatory oligonucleotides are characterized functionally by the ability to induce high levels of interferon-alpha (IFN-α) from plasmacytoid dendritic cells (pDC) and inducing NK cell activation while having minimal effects on B cell activation. Structurally, this class typically has stabilized poly-G sequences at 5' and 3' ends. It also has a palindromic phosphodiester CpG dinucleotide-containing sequence of at least 6 nucleotides, for example but not necessarily, it contains one of the following hexamer palindromes: GACGTC, AGCGCT, or AACGTT described by Yamamoto and colleagues (Yamamoto, S., et al. J. Immunol. 148:4072-6 (1992). A class CpG immunostimulatory oligonucleotides and exemplary sequences of this class have been described in U.S. Pat. No. 6,949,520 and published PCT application PCT/US00/26527 (WO 01/22990), both filed on Sep. 27, 2000.

In some embodiments, the immunogen described herein, or an immunogenic composition or a pharmaceutical composition thereof, is administered to a subject who is also receiving therapy with a second agent (e.g., a second cholesterol-reducing agent). Cholesterol reducing agents include statins, bile acid sequestrants, niacin, fibric acid derivatives, and long chain alpha, omego-dicarboxylic acids. Statins inhibit cholesterol synthesis by blocking HMGCoA, a key enzyme in cholesterol biosynthesis. Examples of statins are lovastatin, pravastatin, atorvastatin, cerivastatin, fluvastatin, and simvastatin.

This disclosure also provides pharmaceutical compositions that includes the antigenic portion of the immunogen (e.g., an ANGPTL antigen) in a formulation in association with one or more pharmaceutically acceptable excipient(s) and, optionally, combined with one or more adjuvants. The term "excipient" is used herein to describe any ingredient other than the active ingredient (i.e., the immunogen). The choice of excipient(s) can depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the active ingredient.

Pharmaceutical compositions and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition may be prepared, packaged, or sold in bulk, as a single unit dose, or as a plurality of single unit doses. As used herein, a "unit dose" is a discrete amount of the pharmaceutical composition including a predetermined amount of the active ingredient. The amount of the active ingredient is generally equal to the dosage of the active ingredient which would be administered to a subject or a convenient fraction of such a dosage such as, for example, one-half or one-third of such a dosage.

Any method that is accepted in the art for administering peptides or proteins may suitably be employed for administering an immunogen as described herein.

A pharmaceutical composition can be formulated for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous, subcutaneous, intradermal and intramuscular routes, even more preferred embodiments are the intramuscular or the subcutaneous routes.

Formulations of a pharmaceutical composition suitable for parenteral administration typically generally include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further include one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which include the active ingredient in microcrystalline form, microparticles, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the antigenic polypeptide (e.g., an ANGPTL polypeptide), either alone or linked to an immunogenic carrier, optionally in combination with one or more adjuvants, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition that includes the immunogen described herein is a formulation as a sterile aqueous solution having a pH that ranges from about 5.0 to about 6.5 and including from about 0.1 mg/mL to about 20 mg/mL of the immunogen, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

The pharmaceutical composition also can be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurized container, pump, spray, atomizer (preferably an atomizer using electrohydrodynamics to produce a fine mist), or nebulizer, with or without the use of a suitable propellant, or as nasal drops.

Prior to use in a dry powder or suspension formulation, the drug product is generally micronized to a size suitable for delivery by inhalation (typically less than 5 microns).

This may be achieved by any appropriate comminuting method, such as spiral jet milling, fluid bed jet milling, supercritical fluid processing to form nanoparticles, high pressure homogenization, or spray drying.

Capsules, blisters, or cartridges for use in an inhaler or insufflator may be formulated to contain a powder mix of the immunogen described herein, a suitable powder base, and a performance modifier.

A suitable solution formulation for use in an atomizer using electrohydrodynamics to produce a fine mist may contain a suitable dose of the immunogen per actuation and the actuation volume may vary from 1 μL to 100 μL.

Suitable flavors, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release. Modified release formulations include delayed release, sustained release, pulsed release, controlled release, targeted release, or programmed release.

In the case of dry powder inhalers and aerosols, the dosage unit is determined by means of a valve which delivers a metered amount. The dosage units in accordance with the methods described herein are typically arranged to administer a metered dose or "puff" of the immunogen. The overall daily dose will typically be administered in a single dose or, more usually, as divided doses throughout the day.

A pharmaceutical composition including the immunogen described herein also may be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compositions described herein can be used to reduce serum triglycerides in a subject at risk or suffering from such disorder or symptom by stimulating an immune response in the subject by immunotherapy. Immunotherapy can include an initial immunization followed by additional (e.g., one, two, three, or more) boosters.

An "immunologically effective amount" of the immunogen, or composition thereof, is an amount that is delivered to a mammalian subject, either in a single dose or as part of a series, which is effective for inducing an immune response in the subject against the protein that can inhibit LPL. This amount varies depending upon the health and physical condition of the individual to be treated, the taxonomic group of the individual to be treated, the capacity of the individual's immune system to synthesize antibodies, the formulation of the vaccine, and other relevant factors. It is expected that the amount will fall in a relatively broad range that can be determined through routine trials.

A "pharmaceutically effective dose" or "therapeutically effective dose" is that dose required to reduce the serum triglycerides level in a subject. The pharmaceutically effective dose depends on inter alia the specific compound to administer, the severity of the symptoms, the susceptibility of the subject to side effects, the type of disease, the composition used, the route of administration, the type of mammal being treated, the physical characteristics of the specific mammal under consideration such as health and physical condition, concurrent medication, the capacity of the individual's immune system to synthesize antibodies, the degree of protection desired, and other factors that those skilled in the medical arts will recognize. For prophylaxis purposes, the amount of peptide in each dose is selected as an amount which induces an immunoprotective response without significant adverse side effects in typical vaccines. Following an initial vaccination, subjects may receive one or several booster immunizations adequately spaced.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For example, the immunogen described herein or a pharmaceutic composition thereof can be administered to a subject at a dose of about 0.1 μg to about 5 mg, e.g., from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, from about 1 mg to about 2 mg, with optional boosters given every, for example, 1 week, 2 weeks, 3 weeks, 4 weeks, two months, three months, 6 months and/or year.

In some embodiments, a single dose of the immunogen described herein or a pharmaceutical composition thereof is administered. In other embodiments, multiple doses of the immunogen described herein or a pharmaceutical composition thereof are administered. The frequency of administration can vary depending on any of a variety of factors, e.g., severity of the symptoms, degree of immunoprotection desired, whether the composition is used for prophylactic or curative purposes, etc. For example, in some embodiments, the immunogen described herein or a pharmaceutical composition thereof is administered once per month, twice per month, three times per month, every other week (qow), once per week (qw), or twice per week (biw). When a pharmaceutical composition is used for prophylaxis purposes, it will generally be administered for both priming and boosting doses. Boosting doses may include the antigenic peptide (e.g., ANGPTL polypeptide) in the absence of the original immunogenic carrier molecule. Such booster constructs may include an alternative immunogenic carrier or may be in the absence of any carrier. Such booster compositions may be formulated either with or without adjuvant.

The duration of administration of the immunogen—e.g., the period of time over which the immunogen is administered—can vary depending on any of a variety of factors, e.g., patient response, etc. For example, the antigenic polypeptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, the immunogen may be administered for the life of the patient.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

What is claimed is:

1. An immunogen comprising:
   a virus-like particle; and
   an antigen linked to the virus-like particle, the antigen comprising an antigenic portion of SEQ ID NO:1.

2. The immunogen of claim 1, wherein the antigen comprises an amino acid sequence having at least 80% sequence similarity to amino acids 32-47 of SEQ ID NO:1.

3. The immunogen of claim 1, wherein the antigen comprises an amino acid sequence having at least 80% sequence similarity to amino acids 32-57 of SEQ ID NO:1.

4. The immunogen of claim 1, wherein the virus-like particle comprises one or more Qbeta coat proteins.

5. The immunogen of claim 4, wherein the antigen is linked to the VLP through a Gly-Gly-Gly-Cys (SEQ ID NO:6) linker at the C-terminal of the antigen.

6. A composition comprising:
   the immunogen of claim 1; and
   a pharmaceutically-acceptable carrier.

7. The composition of claim 6, further comprising an adjuvant.

8. A method of reducing serum triglycerides in a subject, the method comprising administering a therapeutically effective amount of the immunogen of claim 1 to the subject.

9. The method of claim 8, wherein the immunogen is administered in combination with an adjuvant.

10. The method of claim 8, wherein the immunogen is administered in combination with at least one additional therapeutic agent.

11. The method of claim 10, wherein the additional therapeutic agent comprises a statin or a fibric acid derivative.

12. A nucleic acid encoding the immunogen of claim 1.

13. An expression vector comprising the nucleic acid of claim 12.

14. A host cell comprising the expression vector of claim 13.

* * * * *

UNITED STATES PATENT AND TRADEMARK OFFICE
CERTIFICATE OF CORRECTION

PATENT NO. : 11,633,471 B2
APPLICATION NO. : 16/977648
DATED : April 25, 2023
INVENTOR(S) : Bryce Chackerian et al.

Page 1 of 1

It is certified that error appears in the above-identified patent and that said Letters Patent is hereby corrected as shown below:

On the Title Page

In the Applicant item (71), the text should read --UNM Rainforest Innovations, Albuquerque, NM (US); The United States of America, as represented by the Secretary, Department of Health and Human Services, Bethesda, MD (US)--

Signed and Sealed this
Thirtieth Day of January, 2024

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 460
<212> TYPE: PRT
<213> ORGANISM: Homo Sapiens

<400> SEQUENCE: 1

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125
```

Glu Glu Lys Ile Leu Leu Gln Gln Lys Val Lys Tyr Leu Glu Glu Gln
            130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Cys Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 2
<211> LENGTH: 406
<212> TYPE: PRT
<213> ORGANISM: Homo Sapiens

<400> SEQUENCE: 2

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu

```
                    35                  40                  45
Leu Gln Leu Gly Gln Gly Leu Arg Glu His Ala Glu Arg Thr Arg Ser
 50                  55                  60

Gln Leu Ser Ala Leu Glu Arg Arg Leu Ser Ala Cys Gly Ser Ala Cys
 65                  70                  75                  80

Gln Gly Thr Glu Gly Ser Thr Asp Leu Pro Leu Ala Pro Glu Ser Arg
                 85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
            115                 120                 125

His Leu Glu Lys Gln His Leu Arg Ile Gln His Leu Gln Ser Gln Phe
        130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
            195                 200                 205

Ser Pro Pro Phe Leu Val Asn Cys Lys Met Thr Ser Asp Gly Gly Trp
210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
                260                 265                 270

Leu Ala Val Gln Leu Arg Asp Trp Asp Gly Asn Ala Glu Leu Leu Gln
            275                 280                 285

Phe Ser Val His Leu Gly Gly Glu Asp Thr Ala Tyr Ser Leu Gln Leu
290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Ser Gln Tyr Phe Arg Ser Ile Pro
        355                 360                 365

Gln Gln Arg Gln Lys Leu Lys Lys Gly Ile Phe Trp Lys Thr Trp Arg
        370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 3
<211> LENGTH: 198
<212> TYPE: PRT
<213> ORGANISM: Homo Sapiens

<400> SEQUENCE: 3
```

```
Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
            20                  25                  30

Glu Glu Leu Thr Leu Leu Phe His Gly Thr Leu Gln Leu Gly Gln Ala
        35                  40                  45

Leu Asn Gly Val Tyr Arg Thr Thr Glu Gly Arg Leu Thr Lys Ala Arg
    50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
        100                 105                 110

Ala Glu Val Leu Gly Glu Val Ala Gln Ala Gln Lys Val Leu Arg Asp
            115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
        195

<210> SEQ ID NO 4
<211> LENGTH: 84
<212> TYPE: PRT
<213> ORGANISM: Mus Musculus

<400> SEQUENCE: 4

Met His Thr Ile Lys Leu Phe Leu Phe Val Val Pro Leu Val Ile Ala
1               5                   10                  15

Ser Arg Val Asp Pro Asp Leu Ser Ser Phe Asp Ser Ala Pro Ser Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp

<210> SEQ ID NO 5
<211> LENGTH: 82
<212> TYPE: PRT
<213> ORGANISM: Mus Musculus

<400> SEQUENCE: 5

Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
```

```
                35                  40                  45
Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly

<210> SEQ ID NO 6
<211> LENGTH: 4
<212> TYPE: PRT
<213> ORGANISM: Artificial Sequence
<220> FEATURE:
<223> OTHER INFORMATION: Linker

<400> SEQUENCE: 6

Gly Gly Gly Cys
1
```